United States Patent [19]
Kinast

[11] Patent Number: 5,987,343
[45] Date of Patent: Nov. 16, 1999

[54] METHOD FOR STORING PULSE OXIMETRY SENSOR CHARACTERISTICS

[75] Inventor: Eric Kinast, Westwood, N.J.

[73] Assignee: Datascope Investment Corp., Montvale, N.J.

[21] Appl. No.: 08/969,405

[22] Filed: Nov. 7, 1997

[51] Int. Cl.[6] ........................................... A61B 5/00
[52] U.S. Cl. ............................................... 600/323
[58] Field of Search .................................. 600/310, 322, 600/323, 331; 356/39, 41; 250/552, 214 R

[56] References Cited

U.S. PATENT DOCUMENTS

| | | | |
|---|---|---|---|
| 4,446,715 | 5/1984 | Bailey | 73/1 R |
| 4,621,643 | 11/1986 | New, Jr. et al. | 128/633 |
| 4,700,708 | 10/1987 | New, Jr. et al. | 128/633 |
| 4,770,179 | 9/1988 | New, Jr. et al. | 128/633 |
| 5,720,293 | 2/1998 | Quinn et al. | 128/692 |
| 5,758,644 | 6/1998 | Diab et al. | 600/323 |

*Primary Examiner*—Eric F. Winakur
*Attorney, Agent, or Firm*—Abraham P. Ronai

[57] ABSTRACT

A memory unit capable of storing calibration data attached to a probe portion of a pulse oximeter and a connector portion of an intra-aortic balloon catheter.

4 Claims, 3 Drawing Sheets

METHOD FOR STORING PULSE OXIMETRY SENSOR CHARACTERISTICS

BACKGROUND OF THE INVENTION

1. Field of the Invention

The invention relates to a method for storing pulse oximetry sensor and intra-aortic balloon (IAB) catheter characteristics. More particularly, the invention relates to a pulse oximeter probe or an IAB which incorporate a memory unit to store useful parameters.

2. Description of the Prior Art

A pulse oximeter sensor (probe) is a device containing generally two light emitters of differing wavelengths and a photodetector, arranged so as to admit the photodetector to respond to light from the emitters which either diffuses through, or is scattered back by, the tissue of a patient's extremity. The signals, corresponding to the different wavelengths, are analyzed by a companion pulse oximeter instrument, which determines the oxygen saturation of the blood flowing through the tissue. As is the case for any colormetric analysis, the accuracy of the oxygen determination is dependent on the accuracy to which the emitter wavelengths are known. Since the sensors are interchangeable, and often even disposable, accurate results require that the sensors be manufactured with well controlled emitter wavelengths, or that the sensor include a means for encoding the emitter wavelength error, so that the oximeter may apply a calibration correction. Such a means of error coding and correction allows inexpensive LEDs (Light Emitting Diodes), with only loose control of wavelength, to be used as emitters, while still maintaining accurate oximeter response. During manufacture of the sensor, this coding means is arranged to reflect the wavelength error of the LEDs. In operation, the oximeter reads the coding means and applies a suitable correction, as indicated by the coding means, to the oximeter readings, thereby compensating for the LED wavelength errors.

U.S. Pat. Nos. 4,621,643 and 4,700,708 disclose a pulse oximeter which uses resistors or resistance elements, embedded in either the sensor or the sensor's electrical connector, to codify the wavelength error. The error is indicated by the ohmic value of the resistor. A microprocessor, common in all modern pulse oximeters, uses the value of the resistor to choose between a number of different correlation tables, which are necessary in calculating blood oxygenation. A number of correlation tables, each containing data corresponding to a specific wavelength of light, are stored in the microprocessor. The value of the resistor acts as a code, which is interpreted by the microprocessor, indicating the wavelength of light emitted by the specific LED which was consciously paired with the resistor in the probe during manufacture. The resistor is attached to the probe, the detachable probe portion of the pulse oximeter, rather than the oximeter itself, so that probes can be used interchangeably with any compatible pulse oximeter. During use, the resistance of the resistive element in the probe is determined and this value is used by the microprocessor to choose which wavelength correlation table to use in calculating the blood oxygenation of the patient.

During manufacture of such a prior art pulse oximeter, the LEDs are characterized for wavelength and sorted into wavelength groups. Each group is then assembled into sensors bearing a resistor, the value of which is indicative of the particular wavelength group. The process of testing and sorting the LEDs prior to sensor assembly adds considerable material handling burden and cost to the manufacturing process. A more ideal process would feature a memory means which could be adjusted or programmed after the sensor is completely assembled. This would allow the LEDs to be assembled into sensors without the need for pre-testing or sorting. At the final test of the sensor/probe, the wavelengths would be measured, and the appropriate information programmed into the memory means.

A second disadvantage of the resistor coding method is that it encodes only a single parameter, that of the wavelength error. It may be desirable to encode other parameters, such as LED intensity, date of manufacture, sensor type, etc. Additional parameters can be encoded by the use of multiple resistors, but this rapidly becomes unwieldy as the number of parameters increases. An ideal coding means would allow multiple parameters to be encoded in a single device during final test stage at the conclusion of the manufacturing process.

Similar to the pulse oximeter, many intra-aortic balloon (IAB) catheters utilize a resistor to encode operating parameters. Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. A passageway for inflating and deflating the balloon extends through the catheter and is connected at its proximal end to an external pump. The IAB catheter is connected to the pump by means of a connector. An encoding resistor, similar to the one used in the pulse oximeter, is generally embedded in the connector and is used to encode the volume of the IAB balloon.

A disadvantage of the resistor coding method is that it encodes only a single parameter. It may be desirable to encode other parameters, such as IAB dead volume, error detection code, expiration date, flow restriction, helium diffusion rate, membrane thickness, serial number, and configuration. Additional parameters can be encoded by the use of multiple resistors, but this rapidly becomes unwieldy as the number of parameters increases.

While pulse oximeters and IAB catheters incorporating the resistor coding method may be suitable for the particular purpose employed, or for general use, they would not be as suitable for the purposes of the present invention as disclosed hereafter.

SUMMARY OF THE INVENTION

It is an object of the invention to produce a pulse oximeter incorporating an inexpensive method for storing LED wavelength error.

It is another object of the invention to produce a pulse oximeter capable of storing multiple parameters in a single device.

It is a further object of the invention to produce an IAB catheter incorporating an inexpensive method for storing balloon volume.

It is a still further object of the invention to produce an IAB capable of storing multiple parameters in a single device.

The invention is a memory unit capable of storing calibration data attached to a probe portion of a pulse oximeter and the connector portion of an intra-aortic balloon catheter.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
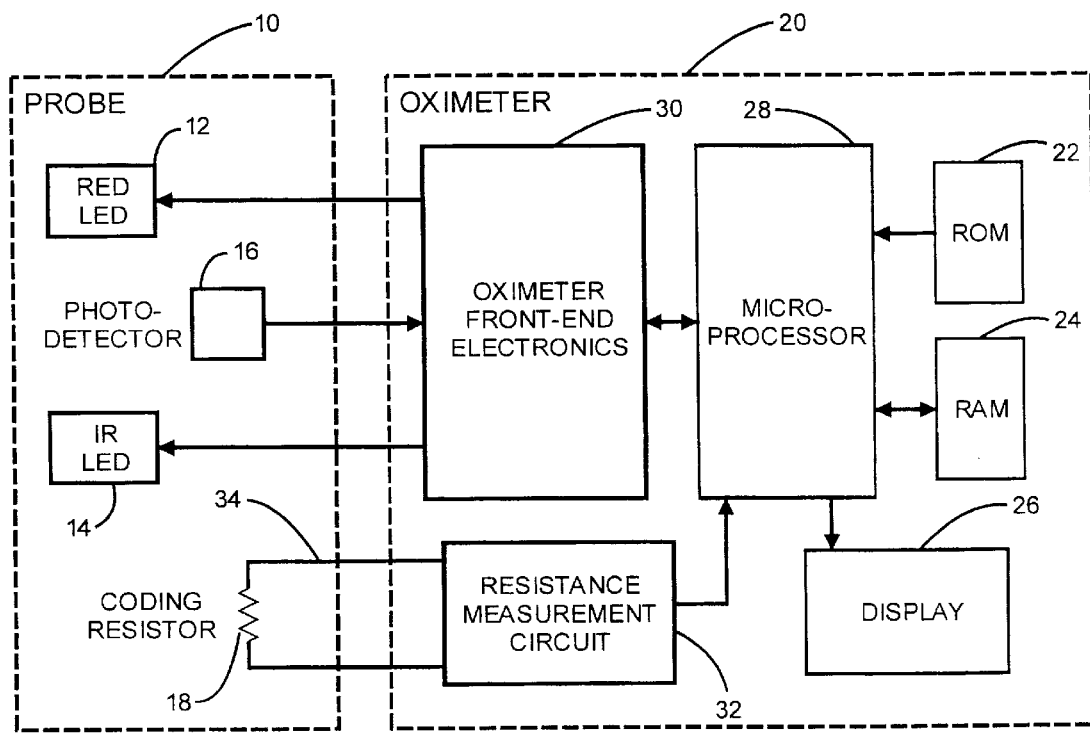
FIG. 1 is a block diagram of a prior art pulse oximeter incorporating the resistor coding method.

FIG. 1 illustrates a block diagram of a prior art pulse oximeter incorporating the resistor coding method. The pulse oximeter has two main components: a probe 10 and a oximeter 20. The probe 10 and the oximeter 20 are circumscribed by a dotted line and are labeled probe and oximeter, respectively. The probe 10 comprises a red LED 12, an IR LED 14, a photodetector 16, and a coding resistor 18. The oximeter 20 comprises a ROM 22, RAM 24, display 26, microprocessor 28, oximeter front-end electronics 30, and a resistance measurement circuit 32. The oximeter front-end electronics 30 accepts input signals from the photodetector 16, and the microprocessor 28, and also outputs signals to the microprocessor 28, the red LED 12, and the IR LED 14. The microprocessor 28 accepts inputs from the oximeter front-end electronics 30, ROM 22, RAM 24, and the resistance measurement circuit 32, and outputs signals to the RAM 24, display 26 and oximeter front-end electronics 30. The coding resistor 18 is connected to a wire 34, said wire 34 being connected to the resistance measurement circuit 32.

During operation the resistance measurement circuit 32 measures the resistance of the resistor 18 and communicates this value to the microprocessor 28. The microprocessor 28 then uses this value to choose between correlation tables, used in calculating blood oxygenation levels, stored in its memory.

Figure 2:
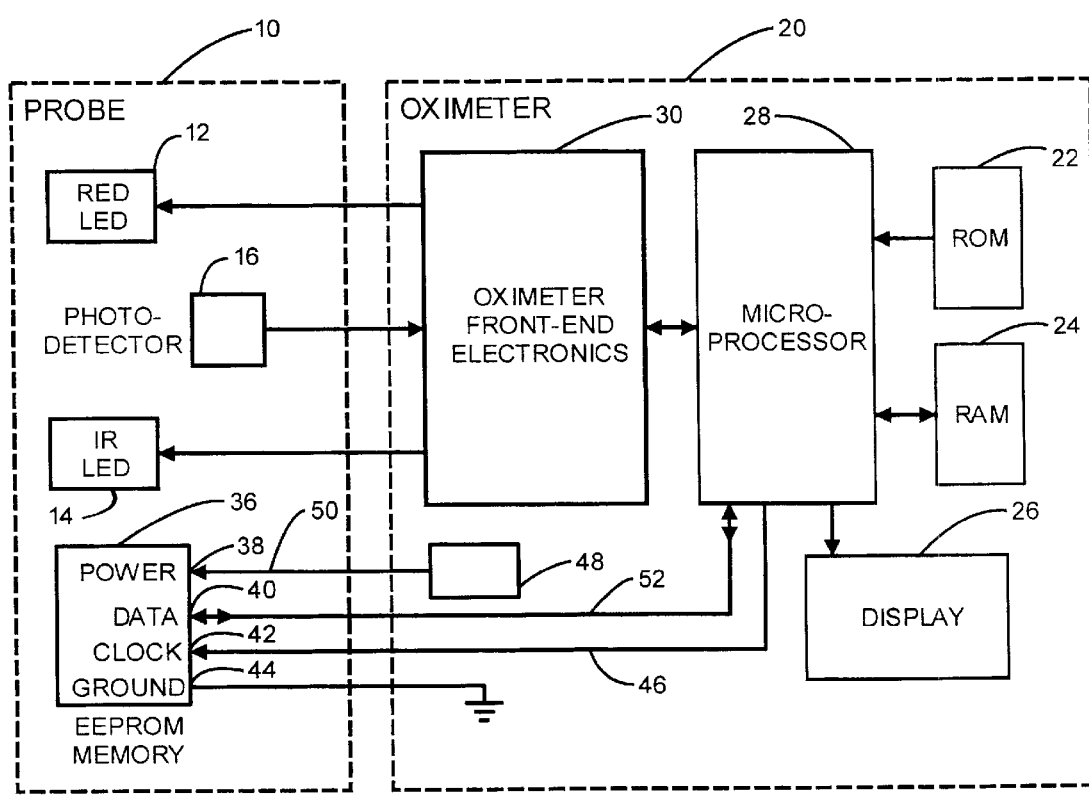
FIG. 2 is block diagram of an improved pulse oximeter wherein the coding resistor of the prior art is replaced with an EEPROM memory unit.

FIG. 2 illustrates the improved pulse oximeter wherein the coding resistor of the prior art is replaced with an EEPROM memory unit 36. Similar to the prior art, the improved pulse oximeter has two main components: a probe 10 and an oximeter 20. The probe 10 and the oximeter 20 are circumscribed by a dotted line and are labeled probe and oximeter, respectively. The probe 10 comprises a red LED 12, an IR LED 14, a photodetector 16, and an EEPROM memory unit 36. The oximeter 20 comprises a ROM 22, RAM 24, display 26, microprocessor 28, oximeter front-end electronics 30, and a power source 48. The oximeter front-end electronics 30 accepts input signals from the photodetector 16, and the microprocessor 28, and also outputs signals to the microprocessor 28, the red LED 12, and the IR LED 14. The EEPROM memory unit 36 has a power port 38, a data port 40, a clock port 42, and a ground port 44 which is connected to ground. The clock port 42 receives a clock signal 46 generated by the microprocessor 28. The power port 38 receives a power signal 50 from the power source 48 which powers the EEPROM memory unit 36. The EEPROM memory unit 36 and the microprocessor 28 communicate via an input/output wire 52 which is connected between the data port 40 of the EEPROM memory unit 36 and the microprocessor 28. The microprocessor 28 accepts input from the oximeter front-end electronics 30, ROM 22, the RAM 24, and the display 26. Note that the EEPROM memory unit 36 can be replaced with any nonvolatile memory.

During operation, the EEPROM memory unit 36 communicates the wavelength error to the microprocessor 28 which uses it to choose between the correlation tables stored within its memory. The microprocessor could also be programmed to write to the EEPROM memory unit 36 and thereby record cumulative hours of operation, number of patient uses, or other data which is of value in administering the use of sensors with limited life.

Figure 3:
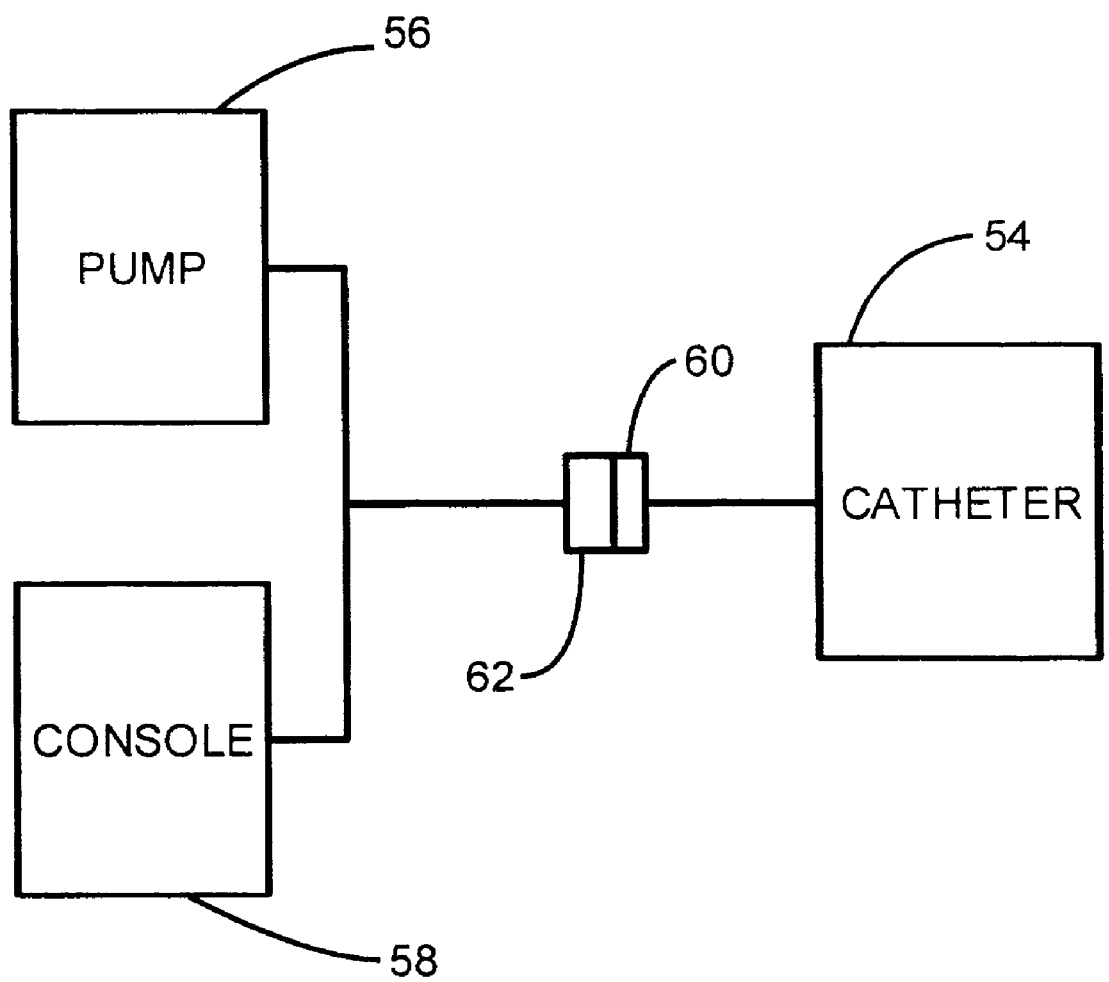
FIG. 3 is a block diagram of a prior art intra-aortic balloon catheter system.

FIG. 3 illustrates a block diagram of a prior art IAB catheter system comprising a catheter 54 having a first connector 60, a pump 56, and a console 58. The pump 56 and the console 58 share a second connector 62. The pump 56 and the console 58 are connected to the first connector 60 of the catheter 54 by means of the second connector 62 which mates with the first connector 60. The console 58 controls the pump 56 and the pump 56 inflates and deflates the catheter 54. A resistor is embedded in the first connector during manufacture of the catheter 54 and first connector 60. During operation the console 58 measures the resistance of the resistor and uses this value to retrieve the volume of the balloon component of the catheter 54 from a table in its memory. This volume value is then used to choose from a choice of pump command scrips a script appropriate for use with the catheter being considered.

The present invention envisions replacing the resistor with a EEPROM memory unit, as was done in the pulse oximeter. Similar to the resistor the EEPROM memory unit is embedded in the first connector 60, as illustrated in FIG. 3, and communicates with the console 58. During operation, the EEPROM memory unit 36 communicates the balloon volume to the console 58. The microprocessor could also be programmed to write to the EEPROM memory unit 36 and thereby record cumulative hours of operation or other data which is of value in administering the use of IAB catheters.

What is claimed is:

1. A pulse oximeter comprising:

a probe portion including two or more electromagnetic radiation emitters, each emitting a different wavelength, and a photodetector arranged to detect radiation emitted from the emitters after it has interacted with a subject, and further including a memory unit for storing data related to said emitters or said photodetector, and an oximeter portion including a control unit in communication with said emitters, said photodetector, and said memory unit, said control unit controlling the emitters and calculating the oxygen saturation from signals obtained from the photodetector, and including means for modifying the data in the memory unit.

2. The pulse oximeter as claimed in claim 1 wherein the memory unit is an EEPROM.

3. A method for modifying data contained in a pulse oximeter, said pulse oximeter comprising a probe portion including two or more electromagnetic radiation emitters, each emitting a different wavelength, and a photodetector arranged to detect radiation emitted from the emitters after it has interacted with a subject, and further including a memory unit for storing data related to said emitters or said photodetector, and an oximeter portion including a control unit in communication with said emitters, said photodetector, and said memory unit, said control unit controlling the emitters and calculating the oxygen saturation from signals obtained from the photodetector, and including means for modifying the data in the memory unit, comprising the steps of:

outputting one or more signals via the control unit to the memory unit to write data in the memory unit, and writing the data in the memory unit in response to said one or more signals.

4. The method for modifying data contained in a pulse oximeter as claimed in claim 3, wherein the memory unit is an EEPROM.

* * * * *